United States Patent
Suriye et al.

(10) Patent No.: US 10,131,594 B2
(45) Date of Patent: Nov. 20, 2018

(54) METATHESIS CATALYST ON MIXED METAL OXIDE-ZEOLITE SUPPORT AND PROCESS FOR USE THEREOF

(71) Applicant: SMH Co., Ltd, Bangkok (TH)

(72) Inventors: Kongkiat Suriye, Samutprakan (TH); Wuttithep Jareewatchara, Bangkok (TH); Pruphanya Lekngarm, Bangkok (TH); Somboon Chaemchuen, Nakhonpathom (TH); Ketsada Sutthiumporn, Chonburi (TH); Anuwat Nonkhamwong, Rayong (TH)

(73) Assignee: SMG Co., Ltd, Bangkok (TH)

(*) Notice: Subject to any disclaimer, the term of this patent is extended or adjusted under 35 U.S.C. 154(b) by 2 days.

(21) Appl. No.: 15/515,732

(22) PCT Filed: Oct. 28, 2014

(86) PCT No.: PCT/TH2014/000051
§ 371 (c)(1),
(2) Date: Mar. 30, 2017

(87) PCT Pub. No.: WO2016/068814
PCT Pub. Date: May 6, 2016

(65) Prior Publication Data
US 2017/0297980 A1    Oct. 19, 2017

(51) Int. Cl.
| | | |
|---|---|---|
| C07C 6/04 | (2006.01) |
| B01J 35/00 | (2006.01) |
| B01J 21/08 | (2006.01) |
| B01J 23/28 | (2006.01) |
| B01J 23/30 | (2006.01) |
| B01J 23/36 | (2006.01) |
| B01J 29/06 | (2006.01) |
| B01J 29/08 | (2006.01) |
| B01J 37/02 | (2006.01) |
| B01J 37/08 | (2006.01) |

(52) U.S. Cl.
CPC ............... *C07C 6/04* (2013.01); *B01J 21/08* (2013.01); *B01J 23/28* (2013.01); *B01J 23/30* (2013.01); *B01J 23/36* (2013.01); *B01J 29/06* (2013.01); *B01J 29/084* (2013.01); *B01J 35/0006* (2013.01); *B01J 37/0201* (2013.01); *B01J 37/0236* (2013.01); *B01J 37/08* (2013.01); *C07C 2521/08* (2013.01); *C07C 2523/30* (2013.01); *C07C 2529/16* (2013.01); *Y02P 20/52* (2015.11)

(58) Field of Classification Search
CPC ....... C07C 6/04; C07C 11/06; C07C 2521/08; C07C 2523/30; C07C 2529/16; B01J 21/08; B01J 23/28; B01J 23/30; B01J 23/36; B01J 29/06; B01J 29/084; B01J 35/0006; B01J 37/0201; B01J 37/0236; B01J 37/08; Y02P 20/52
See application file for complete search history.

(56) References Cited

U.S. PATENT DOCUMENTS

| | | | |
|---|---|---|---|
| 4,522,936 A | 6/1985 | Kukes et al. | |
| 4,575,575 A | 3/1986 | Drake et al. | |
| 5,120,894 A | 6/1992 | McCauley | |
| 6,433,240 B1* | 8/2002 | Schwab | B01D 3/141 585/313 |
| 2001/0003140 A1* | 6/2001 | Schwab | B01D 3/141 585/644 |
| 2002/0002317 A1* | 1/2002 | Schwab | C07C 7/163 585/643 |
| 2010/0145126 A1 | 6/2010 | Takai et al. | |
| 2010/0167911 A1 | 7/2010 | Shum | |
| 2011/0077444 A1 | 3/2011 | Butler | |
| 2011/0253596 A1 | 10/2011 | Khabashesku et al. | |
| 2013/0230441 A1 | 9/2013 | Hihara et al. | |

FOREIGN PATENT DOCUMENTS

| | | | | |
|---|---|---|---|---|
| EP | 0276096 A1 * | 7/1988 | | C07C 6/04 |
| EP | 0437877 A1 | 7/1991 | | |
| EP | 2151424 A1 | 2/2010 | | |
| EP | 2786978 A1 * | 10/2014 | | B01J 21/10 |
| EP | 2786978 A1 | 10/2014 | | |
| WO | 2016/120423 A1 | 8/2016 | | |
| WO | 2016/150794 A1 | 9/2016 | | |

OTHER PUBLICATIONS

Wolfgang Lutz: "Zeolite Y: Synthesis, Modification, and Properties—A Case Revisited," Advances in Materials Science and Engineering, vol. 2014, 724248, May 22, 2014.

(Continued)

*Primary Examiner* — Sharon Pregler
(74) *Attorney, Agent, or Firm* — Banner & Witcoff, Ltd.

(57) ABSTRACT

The present invention relates to catalyst comprising at least one transition metal selected from Group VIA and Group VIIA metals and a support containing a mixture of 0.1 to 60 percent by weight of zeolite, based on total weight of the support, with at least one other inorganic or organic material, wherein the at least one other inorganic or organic material is selected from silicon dioxide, titanium dioxide, zirconium dioxide and activated carbon, preferably silicon dioxide; and a process for olefin metathesis utilizing that catalyst.

19 Claims, No Drawings

(56) References Cited

OTHER PUBLICATIONS

L. B. McCusker, F. Liebau, and G. Englehardt—IUPAC Recommendations 2001—Pure and Applied Chemistry 73(2)—The Schientific Journal of IUPAC—Jan. 1, 2001.
H. Liu et al. (Journal of Natural Gas Chemistry 18 (2009), p. 331-336).
Banks et al. (Journal of Molecular Catalysis 28 (1-3) (1985) p. 117-131).
S. Huang et al. (Journal of Molecular Catalysis A: Chemical 226 (2005), p. 61-68).
A. Spamer et al. (Applied Catalysis A: General 255 (2013), p. 133-142).
International Search Report and Written Opinion—PCT/TH2014/000051—dated Aug. 21, 2015.
S. Liu et al. (Journal of Natural Gas Chemistry 19 (2010), p. 482-486).
S. Huang et al. (Applied Catalysis A: General 404 (2011), p. 113-119).

* cited by examiner

US 10,131,594 B2

METATHESIS CATALYST ON MIXED METAL OXIDE-ZEOLITE SUPPORT AND PROCESS FOR USE THEREOF

CROSS-REFERENCE TO RELATED APPLICATIONS

This application is a U.S. National Stage application under 35 U.S.C. § 371 of International Application PCT/TH2014/000051 (published as WO 2016/068814 A1), filed Oct. 28, 2014. Benefit of the filing date of this prior application is hereby claimed. This prior application is hereby incorporated by reference in its entirety.

TECHNICAL FIELD

The present invention relates to a metathesis catalyst, as well as to a process for olefin metathesis reaction using the catalyst.

BACKGROUND ART

The olefin metathesis reaction, also known as dismutation and disproportionation of olefins, is a reaction of a great practical interest. The reaction generally involves redistribution of alkylene fragments by the scission of carbon-carbon double bonds in olefins. By catalyzing the reaction, pairs of carbon-carbon bonds can be reorganized in a statistical manner to transform simple molecules into molecules with desirable properties.

Various catalysts have been developed to improve catalytic performance in metathesis reaction.

For example, US 2010/0145126 A2 describes a catalyst containing a transition metal on a support mixed with a co-catalyst containing Group IA, IIA, IIB, or IIIA metal on a support for use in a process of producing olefins by metathesis reaction. The reaction is required to be carried out in the presence of hydrogen, which is an expensive feedstock and requires a lot of cautions to deal with. In addition, the presence of hydrogen induces hydrogenation to occur as a side reaction which leads to poor propylene selectivity.

Moreover, S. Huang et al. (Journal of Molecular Catalysis A: Chemical 226 (2005), 61-68) and H. Liu et al. (Journal of Natural Gas Chemistry 18(2009), 331-336) studied the use of tungsten oxide on alumina-zeolite support for olefin metathesis catalyst and S. Liu et al. (Journal of Natural Gas Chemistry 19 (2010), 482-486) and S. Huang et al. (Applied Catalysis A: General 404(2011), 113-119) studied the use of molybdenum oxide on alumina-zeolite support. They explained that adding zeolite to alumina support increases Brönsted acidity of the catalyst which results in improved conversion and selectivity in metathesis reaction of ethylene and butene to produce propylene. However, these catalysts suffer from rapid deactivation due to accumulation of coke species.

SUMMARY OF INVENTION

Therefore, it is an object of the present invention to overcome the drawbacks of the prior art by providing a catalyst and a process using thereof which exhibit good catalytic efficiency, especially with improved selectivity and catalytic stability in olefin metathesis reaction.

The above object is achieved by a catalyst comprising at least one transition metal selected from Group VIA and Group VIIA metals and a support containing a mixture of 0.1 to 60 percent by weight of zeolite, based on total weight of the support, with at least one other inorganic or organic material, wherein the at least one other inorganic or organic material is selected from silicon dioxide, titanium dioxide, zirconium dioxide and activated carbon, preferably silicon dioxide.

DESCRIPTION OF EMBODIMENTS

The term Group VIA and Group VIIA metals refers to Group VIA and Group VIIA of the Periodic Table of Element which include chromium, molybdenum, tungsten, manganese, technetium and rhenium. In a preferred embodiment, the at least one transition metal is selected from rhenium, molybdenum and tungsten, more preferably tungsten.

The amount of transition metal used in the catalyst according to the present invention can be widely varied in accordance with the catalytic activity desired. It is preferred that the catalyst comprises the transition metal in an amount of 1 to 12 percent by weight (calculated as elemental metal) of the total catalyst, preferably 5 to 10 percent by weight.

The transition metal component may be present as elemental metal and/or one or more compounds of the metal such as oxide, hydride or sulfide, preferably oxide. And the transition metal can have zero valent or any higher oxidation state.

The term zeolite refers to a particular group of aluminosilicates. These zeolites exhibit a network of $SiO_4$ and $AlO_4$ tetrahedra in which aluminum and silicon atoms are cross-linked in a three-dimensional framework by sharing oxygen atoms. In the framework, the ratio of oxygen atoms to the total of aluminum and silicon atoms may be equal to 2. The framework exhibits a negative electrovalence that typically is balanced by the inclusion of cations within the crystal such as metals, alkali metals, alkaline earth metals or hydrogen.

Zeolites useful in the present invention include large, intermediate and small pore size zeolites and can be naturally occurring or synthetic. Examples of these zeolites include zeolites with structure type of FAU, FER, MWW, MOR, BEA, LTL, MFI and any combination thereof Details of these nomenclatures can be found in IUPAC Recommendations 2001 published in *Pure Appl. Chem* 73(2), pp. 381-394, 2001.

It is preferred for the present invention that the zeolite is selected from ZSM-5, Ferrierite, X-zeolite, Y-zeolite, beta-zeolite and MCM-22, preferably Ferrierite, X-zeolite or Y-zeolite, more preferably Y-zeolite.

It is also preferred that zeolite has silica to alumina mole ratio in the range of 2 to 500, preferably 10 to 200, more preferably 12 to 20, most preferably 14 to 18.

Content of zeolite added to the support effects catalyst performance. Too low amount of zeolite does not give significant improvement to the conversion and selectivity. On the other hand, too high amount of zeolite may results in relatively low catalytic stability.

It is preferred that the support comprises zeolite in an amount of 0.1 to 30 percent by weight of the total support, preferably 0.5 to 20 percent by weight, more preferably 1 to 10 percent by weight, most preferably 4 to 8 percent by weight.

In some embodiments, the at least one other inorganic or organic material may be nanocrystals or nanoparticles of silicon dioxide having size within a range of 1 nm to 100 nm.

The catalyst may also contain at least one lanthanide metal in a suitable amount to improve the effectiveness of the catalyst. Lanthanide metal in the present invention refers to the lanthanide group of the Periodic Table of Element. It includes any of the chemically related elements with atomic numbers 57 to 71, also known as rare-earth or rare-earth elements. In one embodiment, the at least one lanthanide metal is selected from lanthanum, cerium, praseodymium, neodymium, samarium and gadolinium, preferably lanthanum. The presence of at least one lanthanide metal can have an advantageous effect on activity and selectivity of the olefin metathesis catalyst.

The inventive catalyst may be further mixed with any suitable binders, and then formed into any desired shapes, for example, spherical, extrudate, pellets or ring, by extrusion or other suitable methods.

The inventive catalyst can be prepared by various techniques. In an embodiment, the inventive catalyst may be prepared by the following steps:
  a) mixing a suitable amount of zeolite with at least one other inorganic or organic material;
  b) contacting the product obtained from step a) with at least one transition metal compound and at least one solvent; and
  c) drying and/or calcining the product obtained from step b).

Preferably, mixing is carried out by physically mixing. More particularly, mixing is carried out by putting together a solid form of zeolite and a solid form of the at least one other inorganic or organic material at a calculated weight ratio, and then blend them by stirring or shaking until a substantially uniform mixture is achieved.

It is preferred that the zeolite used in step a) is selected from HY-zeolite, NaY-zeolite and $NH_4$Y-zeolite, preferably HY-zeolite.

Further, it is also preferred that the at least one other inorganic or organic material in step a) is silica gel.

Manners for contacting the prepared support with a solution of the transition metal compound can be variously chosen from many of well-known techniques such as, for example, impregnation, co-precipitation, incipient wetness and ion exchange. In some embodiments, it is preferred that the contacting in step b) is carried out by impregnation technique.

There are many possible selections of transition metal compound for the present invention such as oxides, halides, sulfates, nitrates, salts or sulfides of the transition metal. It is preferred that the at least one transition metal compound is ammonium metatungsten tetrahydrate.

The selected solvent for the present invention can be any proper solvent which can dissolve or disperse the selected metal compound such as oxygenated solvent and hydrocarbon solvent. For example, the solvent can be selected from water, methanol, ethanol and hexane. It is preferred that the solvent is water.

Following step a) and b), drying may be performed to remove any excess liquid. Any suitable means, as well known by those skilled in the art, may be employed such as oven drying, passing vigorous stream of any dry gas over the subject to be dried, and the like. The duration of the drying step may vary between a few minutes to several hours. Preferably, it should be carried out for at least a period of time sufficient to effect removal of some or all the excess liquid. Typically less time is required at higher temperature and vice versa. It is preferred that drying is performed for a period of 2 to 24 hours.

Temperature for drying can range from room temperature to any higher temperature which is capable of evaporating liquid without inducing conversion or transformation of catalyst support and metal compound present in the catalyst. It is preferred that drying is carried out at a temperature in the range of 20° C. to 200° C.

The drying may be performed under the atmosphere of any gas which does not react with the catalyst or a component of the catalyst under the selected condition for drying, for example, air, nitrogen, argon, methane and hydrogen. It is preferred that drying is carried out under air or nitrogen.

When necessary, calcining can be preformed after step a) and b) of the preparation steps. Calcining comprises treating the prepared catalyst under a controlled condition and atmosphere suitable for thermal decomposition and removal of volatile fraction of metal compounds. The volatile fraction refers to the anionic ligands part of the compound which is decomposable into gaseous compounds. It is preferred that calcining is carried out at a temperature in the range of 200° C. to 800° C. It is also preferred that calcining is carried out for a period in the range of 1 to 24 hours, more preferably 5 to 10 hours.

Inert gas, oxidizing gas, reducing gas and any combination thereof may be present in the calcining step in order to create a suitable atmosphere. In a particular embodiment, calcining is carried out under air.

The object of the present invention is also achieved by a process for olefin metathesis reaction comprising the following steps:
  a) providing the inventive catalyst;
  b) optionally activating the catalyst of step a); and
  c) contacting the catalyst of step a) or b) with a feed stream of olefin.

The feed stream can optionally contact with a co-catalyst such as, for example, an olefin isomerization catalyst prior to or simultaneously with contacting with the inventive catalyst. Isomerization catalyst can be helpful in a process for olefin metathesis because it promotes the conversion of a less active component presents in the feed stream into a more active component. For example, isomerization catalyst promotes the conversion of 1-butene to 2-butene which is more active in olefin metathesis to produce propylene. Catalysts which are active for the olefin isomerization are of generally known type and can be combined with the inventive catalyst in many different manners. In this regard, reference is made to U.S. Pat. No. 4,575,575, U.S. Pat. No. 5,120,894, U.S. Pat. App. Pub. No. 2011/0077444A1 and Journal of Molecular Catalysis 28(1995) 117-131.

The inventive catalyst can advantageously be activated before contacting with the feed stream. In one embodiment, the inventive catalyst is activated by a method comprising treating the catalyst at a temperature in the range of 200° C. to 700° C. The activation method generally involves heating the catalyst to an elevated temperature under a controlled atmosphere for a length of time sufficient to activate the catalyst. For examples of activation method useful for the present invention, reference is made to U.S. Pat. No. 4,575,575, European Pat. App. Pub. No. 2151424A1, U.S. Pat. App. Pub. No. 2010/0167911A1 and Applied Catalysis A: General 255(2003) 133-142.

Contacting the catalyst and the feed stream preferably comprises contacting a solid phase catalyst with a gaseous feed stream.

The reaction temperature employed can vary depending upon the catalyst and feed(s) employed. Preferably, contacting the catalyst and the feed stream is carried out at a temperature in the range of 200° C. to 600° C., more preferably 250° C. to 550° C., most preferably 350° C. to 450° C.

Pressure during contacting the catalyst and the feed stream can widely vary. For example, pressure in the range of 1 atm to 60 atm, preferably 20 atm to 40 atm can be employed.

A WHSV in the range of 0.01 hr$^{-1}$ to 200 hr$^{-1}$, preferably 0.05 hr$^{-1}$ to 100 hr$^{-1}$, can be chosen during contacting the catalyst and the feed stream to obtain reasonable yield depending upon temperature, pressure and several other factors. The term WHSV refers to Weight Hourly Space Velocity. It can be calculated from mass flow rate of the feed stream divided by weight of catalyst used in the reaction.

For the present invention, feed stream may be one or more hydrocarbon stream comprising at least some unsaturated molecules, for example, aromatic, cyclic, diolefin or olefin. Preferably, the feed stream is C2 to C5 hydrocarbon stream comprising at least some unsaturated molecules. More preferably, the feed stream comprises an olefin selected from the group consisting of C2 olefin, C3 olefin, C4 olefin, C5 olefin and mixtures thereof.

In an embodiment, the feed stream comprises at least a first olefin and at least a second olefin. Preferably, the first olefin and the second olefin are selected from ethylene and 2-butene or ethylene and 2-pentene, preferably ethylene and 2-butene.

Alternatively, the process further comprises, after step c), a regeneration step.

When the inventive catalyst has been employed in the reaction process and has lost its activity due to the buildup of poisonous substances, coke, carbon and/or polymer on the catalyst surface, it can undergo regeneration. In the process of regeneration, the poisonous substances, coke, carbon and/or polymer deposited on the catalyst is substantially removed. It is important to control condition of the regeneration step so that a satisfying level of coke removal is achieved while pore structure, active sites and other original catalytic functions are not excessively altered or destroyed. Examples of regeneration process which can be used with the inventive catalyst can be found in Applied Catalysis A: General 255(2003) 133-142, U.S. Pat. App. Pub. No. 2010/0167911A1 and U.S. Pat. No. 4,522,936.

Surprisingly, it was found that the inventive catalyst, as well as the inventive process, provides high yield, high selectivity as well as high catalytic stability in olefin metathesis reaction.

EXAMPLES

The following examples are intended to be illustrative of this invention only. They are not to be taken in any way limiting on the scope of this invention. Numerous changes and modifications can be made without departing from the scope of the invention as disclosed in the accompanying claims Example 1 (Catalyst Preparation)

A catalyst according to the present invention was prepared by first physically mixing 90 wt % of silica gel with 10 wt % of HY-zeolite and then impregnating an aqueous solution containing a pre-calculated amount of ammonium metatungsten tetrahydrate onto the mixture of silica gel and HY-zeolite. The obtained mixture was left for 2 hours at ambient atmosphere prior to drying at 110° C. in an oven overnight. The final dried mixture appeared as a white solid. Next, the white solid mixture was calcined in air at 500° C. for 8 hours to obtain the final catalyst ready to be used in metathesis reaction.

Example 2 (Conversion and Selectivity Test)

Catalyst samples were subjected to conversion and selectivity test. The samples include:

Sample A which comprises tungsten oxide on a support comprising a mixture of 90 wt % of silica and 10% wt of Y-zeoltie, Sample B which comprises tungsten oxide on a silica support, and Sample C which comprises tungsten oxide on a silica support modified with 0.5 wt % of lanthanum, wherein all samples A to C contain the same amount of tungsten oxide.

Sample A, Sample B and Sample C were treated prior to testing by packing 3 grams of catalyst in a reactor then heating the catalyst to 500° C. for 1 hour under nitrogen flow. Subsequently, the metathesis reaction of ethylene and another feed stream containing 1-butene, 2-butene, isobutene and other paraffins was performed over the catalyst mixture at temperature 350° C.

Effluents from the reaction were directed to GC-FID (Agilent) to measure their chemical composition. The measured compositions of effluents were used to calculate butene conversion and propylene selectivity. Percent butene conversion was calculated from weight of 1-butene and 2-butene converted during reaction divided by weight of 1-butene and 2-butene in feed stream and then multiplies by one hundred. And percent propylene selectivity was calculated from weight of propylene produced from the reaction divided by weight of all product produced from the reaction and then multiplies by one hundred. The results are shown in Table 1.

TABLE 1

| Sample | % butene conversion | | | % propylene selectivity | | |
|---|---|---|---|---|---|---|
| | SOR* | EOR** | % decrease | SOR* | EOR** | % decrease |
| A | 75.9 | 75.0 | 1.18 | 92.4 | 92.8 | −0.43 |
| B | 38.4 | 32.8 | 14.58 | 74.1 | 65.1 | 12.15 |
| C | 70.4 | 40.0 | 43.18 | 86.8 | 77.6 | 10.6 |

*SOR = Start of Run (2 hours from start of reaction)
**EOR = End of Run (24 hours from start of reaction)

As demonstrated by the result above, Sample A, which is the catalyst according to the present invention, provides higher butene conversion and higher propylene selectivity than Sample B and C. Moreover, catalytic stability of Sample A evidently shows less decrease of conversion and selectivity from SOR to EOR than other samples.

Example 3 (Effect of Zeolite Content and Si/Al of Zeolite Used in the Support)

Catalyst samples containing a fixed amount of tungsten oxide on supports containing silica and Y-zeolite were prepared from Y-zeolite with various ratios of silica to alumina and at different amount of Y-zeolite in the support. These samples were tested at reaction condition described in Example 2. The results of this test are shown in Table 2.

TABLE 2

| Amount of Y-zeolite in support (wt %) | Si/Al of Y-zeolite in support | % butene conversion | % propylene selectivity | Catalytic stability |
|---|---|---|---|---|
| 0 (100 wt % silica) | 0 | Poor | Poor | Poor |
| 5 | 10 | Excellent | Moderate | Moderate |
| 5 | 15 | Excellent | Excellent | Excellent |
| 5 | 200 | Moderate | Excellent | Excellent |
| 10 | 10 | Excellent | Moderate | Excellent |
| 10 | 15 | Excellent | Excellent | Excellent |
| 10 | 200 | Moderate | Excellent | Excellent |
| 20 | 10 | Excellent | Moderate | Moderate |
| 20 | 15 | Excellent | Moderate | Moderate |
| 20 | 200 | Moderate | Moderate | Moderate |

Poor butene conversion implies that less than 30 percent by weight of butene in the feed stream was consumed in the reaction. Moderate butene conversion implies that 30 to 60 percent by weight of butene in the feed stream was consumed in the reaction. And excellent butene conversion implies that more than 60 percent by weight of butene in the feed stream was consumed in the reaction.

Poor propylene selectivity implies that propylene produced from the reaction was less than 30 percent by weight of the total product. Moderate propylene selectivity implies that propylene produced from the reaction was between 30 and 60 percent by weight of the total product. And excellent propylene selectivity implies that propylene produced from the reaction was more than 60 percent by weight of the total product.

Poor catalytic stability implies that butene conversion dropped greater than 60 percent from start of run to end of run. Moderate catalytic stability implies that butene conversion dropped between 20 to 60 percent from start of run to end of run. And excellent catalytic stability implies that butene conversion dropped less than 20 percent from start of run to end of run.

Evidently, results displayed in Table 2 show that adding zeolite to the silica support has favorable effect on conversion, selectivity and stability of the catalyst for metathesis of olefin. Moreover, it can also be seen that amount and property of zeolite added should be carefully chosen in order to achieve the best result.

The feature disclosed in the foregoing description and in the claims may, both separately and in any combination thereof, be material for realizing the invention in diverse forms thereof.

INDUSTRIAL APPLICABILITY

This has been described in the Description of Embodiments.

The invention claimed is:

1. A process for performing an olefin metathesis reaction, the process comprising
    contacting a catalyst with a feed stream comprising ethylene and a second olefin that is 2-butene or 2-pentene, to produce an olefin metathesis product comprising at least 30 percent by weight propylene, resulting from conversion of ethylene and the second olefin by the olefin metathesis reaction,
    Wherein the catalyst comprises at least one transition metal selected from Group VIA and Group VIIA metals and a support containing a mixture of 0.1 to 60 percent by weight of a zeolite, based on total weight of the support, and at least one other inorganic or organic material selected from the group consisting of silicon, dioxide, titanium dioxide, zirconium dioxide and activated carbon.

2. The process of claim 1, wherein the at least one transition metal is selected from the group consisting of rhenium, molybdenum and tungsten.

3. The process of claim 1, wherein the catalyst comprises the at least one transition metal in an amount of 1 to 12 percent by weight of the catalyst.

4. The process of claim 1, wherein the zeolite is selected from the group consisting of ZSM-5, Ferrierite, X-zeolite, Y-zeolite, beta-zeolite, MCM-22, and mixtures thereof.

5. The process of claim 1, wherein the support comprises the zeolite in an amount of 0.1 to 30 percent by weight of the support.

6. The process of claim 1, wherein the zeolite has a silica to alumina molar ratio of 2 to 500.

7. The process of claim 1, wherein the catalyst further comprises a lanthanide metal.

8. The process of claim 1, further comprising activating the catalyst, prior to contacting it with the feed stream.

9. The process according to claim 8 wherein activating the catalyst comprises treating the catalyst at a temperature in the range of 200° C. to 700° C.

10. The process according to claim 1 wherein contacting the catalyst and the feed stream is carried out at a temperature in the range of 200° C. to 600° C.

11. The process of claim 1, wherein the second olefin is 2-butene.

12. The process of claim 11 wherein the feed stream comprises ethylene and a mixture of 2-butene and 2-pentene.

13. The process according to claim 1, further comprising, following contacting the catalyst with the feed stream, regenerating the catalyst.

14. The process of claim 1, wherein the at least one other inorganic or organic material is silicon dioxide.

15. The process of claim 2, wherein the at least one transition metal is tungsten.

16. The process of claim 4, wherein the zeolite is selected from the group consisting of Ferrierite, X-zeolite, Y-zeolite, and mixtures thereof.

17. The process of claim 16 wherein the zeolite is Y-zeolite.

18. The process of claim 5 wherein the support comprises the zeolite in an amount of 1 to 10 percent by weight of the support.

19. The process of claim 1, wherein the olefin metathesis product comprises at least 60 percent by weight propylene.

* * * * *

UNITED STATES PATENT AND TRADEMARK OFFICE
CERTIFICATE OF CORRECTION

PATENT NO. : 10,131,594 B2
APPLICATION NO. : 15/515732
DATED : November 20, 2018
INVENTOR(S) : Kongkiat Suriye et al.

Page 1 of 1

It is certified that error appears in the above-identified patent and that said Letters Patent is hereby corrected as shown below:

On the Title Page

Under Assignee, Item (73):
Please delete "SMG Co., Ltd" and insert --SMH Co., Ltd--

Signed and Sealed this
Nineteenth Day of March, 2019

Andrei Iancu
*Director of the United States Patent and Trademark Office*